United States Patent [19]

Fogarty et al.

[11] Patent Number: 5,392,783
[45] Date of Patent: Feb. 28, 1995

[54] ADHESIVE TAPE STRIP

[75] Inventors: Thomas J. Fogarty, 5660 Alpine Rd., Portola Valley, Calif. 94028; Thomas A. Howell, Palo Alto, Calif.; Kenneth H. Mollenauer, Santa Clara, Calif.; Michelle Y. Monfort, Los Gatos, Calif.

[73] Assignee: Thomas J. Fogarty, Palo Alto, Calif.

[21] Appl. No.: 80,359

[22] Filed: Jun. 21, 1993

Related U.S. Application Data

[63] Continuation of Ser. No. 641,590, Jan. 15, 1991, abandoned.

[51] Int. Cl.$^6$ ............................................. A61F 13/02
[52] U.S. Cl. .................................. 128/687; 206/411; 156/584; 156/349; 428/40
[58] Field of Search ........................ 206/411, 412, 491; 224/901

[56] References Cited

U.S. PATENT DOCUMENTS

| | | | |
|---|---|---|---|
| 1,208,313 | 12/1916 | Haydon . | |
| 2,172,455 | 9/1939 | Samuel | 128/156 |
| 2,292,272 | 8/1942 | Hirschfield | 40/02 |
| 2,652,829 | 9/1953 | Frieberger | 128/170 |
| 2,815,752 | 12/1957 | Forman | 128/170 |
| 3,032,181 | 5/1962 | Hutter | 206/411 |
| 3,490,448 | 1/1970 | Grubb | 128/156 |
| 3,899,077 | 8/1975 | Spiegelberg | 206/441 |
| 4,090,504 | 5/1978 | Nathan | 128/2.05 R |
| 4,194,618 | 3/1980 | Malloy | 206/411 |
| 4,235,337 | 11/1980 | Dotta | 206/441 |
| 4,265,234 | 5/1981 | Schaar | 206/441 |
| 4,406,290 | 9/1983 | Walbeoffe-Wilson et al. | 128/689 |
| 4,418,822 | 12/1983 | Dotta | 206/441 |
| 4,512,462 | 4/1985 | Dills | 206/411 |
| 4,815,457 | 3/1989 | Mazars et al. | 128/155 |
| 4,884,563 | 12/1989 | Sessions | 206/441 |

Primary Examiner—William E. Kamm
Assistant Examiner—Robert L. Nasser, Jr.
Attorney, Agent, or Firm—Limbach & Limbach

[57] ABSTRACT

An adjustable sensor retainer and method for adjustably securing and retaining a sensor (e.g. a piezoelectric pulse sensor) against a skin region of a person includes the use of a primary retainer tape and an adjustable secondary retainer tape. The primary retainer tape is an adhesive tape to which the sensor can be attached. The adhesive primary retainer tape has strips of protective film with blind pull tabs attached thereto. This allows simplified one-handed application of the primary retainer tape while initially positioning and holding the sensor in place with the other hand. The secondary retainer tape is a tape strip removably attached to the top of the primary retainer tape and disposed over the sensor. After the initial positioning of the sensor with the primary retainer tape, the sensor can be finally positioned and the secondary retainer tape re-attached to the top of the primary retainer tape, thereby securing the sensor in the final desired location. Further, the secondary retainer tape can easily be detached and re-attached to slightly reposition the sensor, as desired.

2 Claims, 2 Drawing Sheets

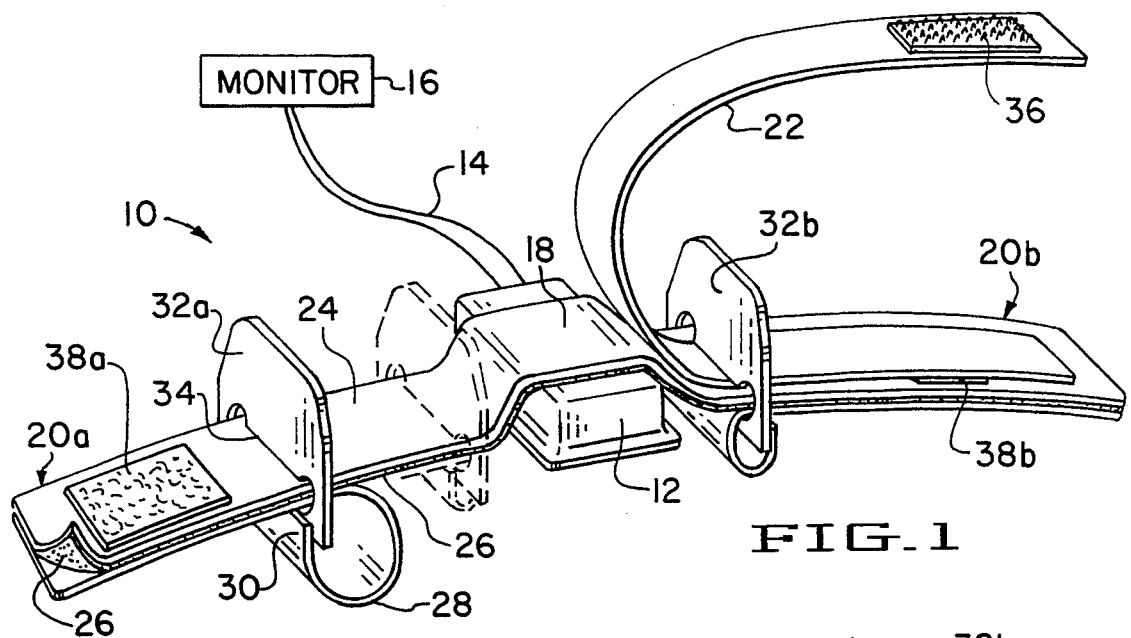
FIG_1
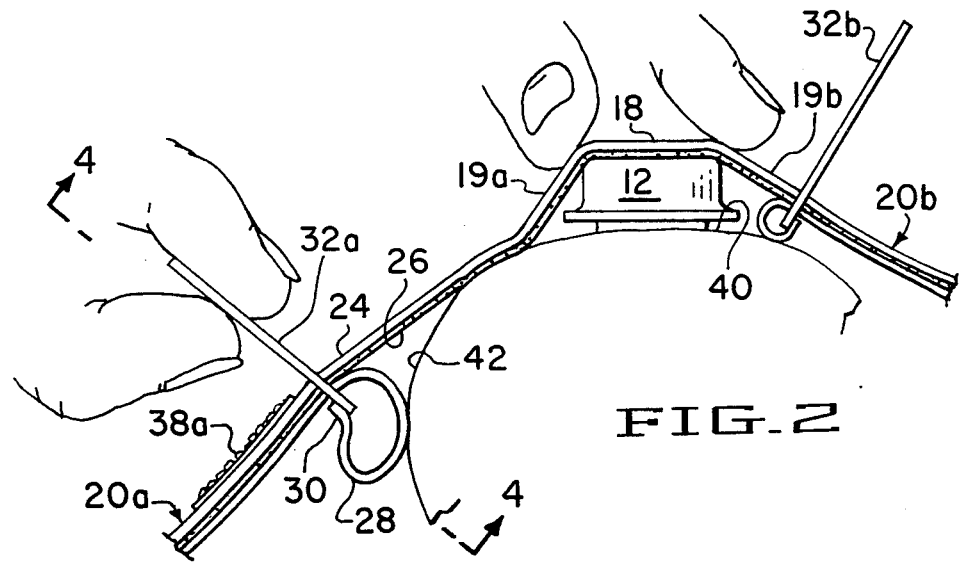
FIG_2
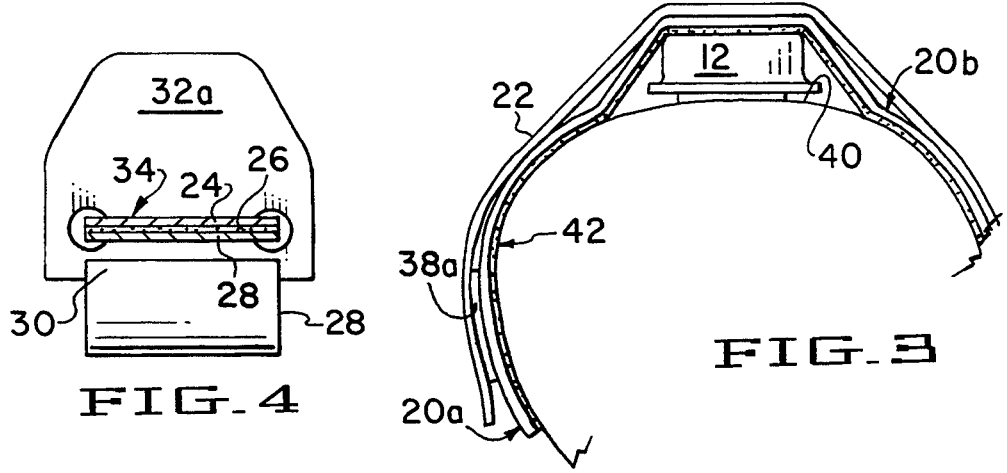
FIG_4
FIG_3

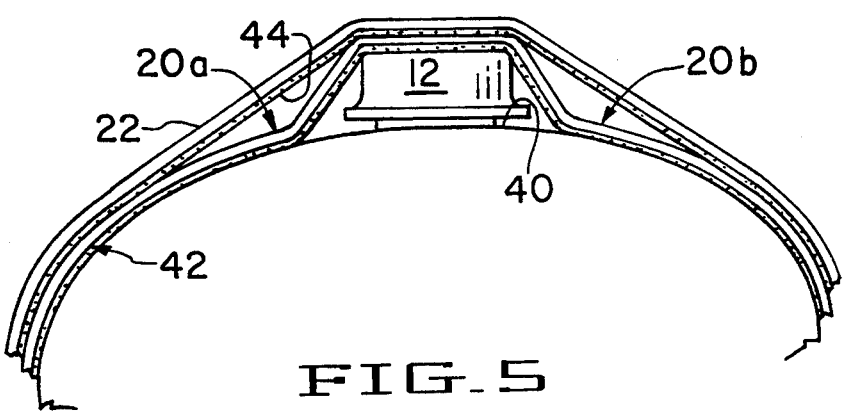
FIG_5
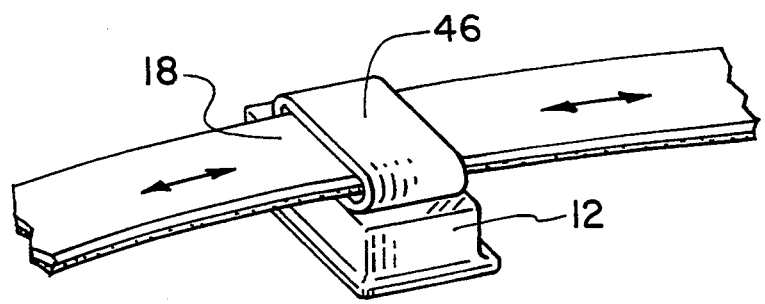
FIG_6
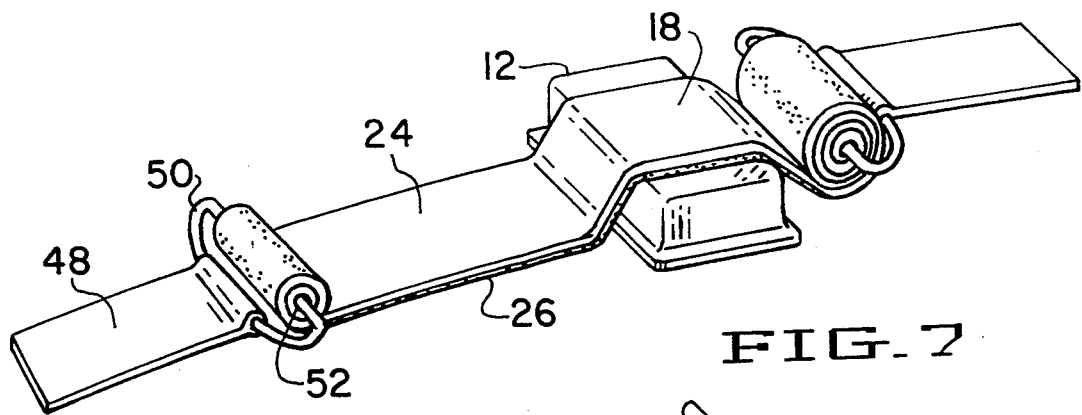
FIG_7
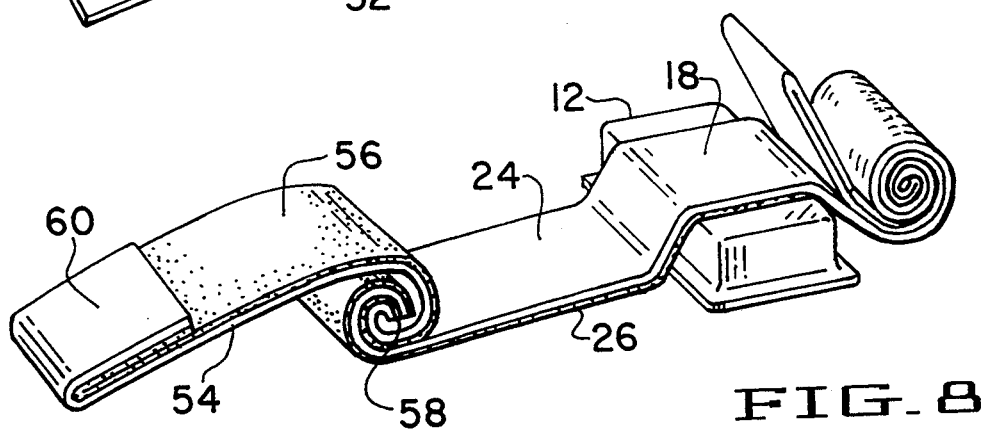
FIG_8

ADHESIVE TAPE STRIP

This is a continuation of application Ser. No. 07/641,590, filed on Jan. 15, 1991, now abandoned.

BACKGROUND OF THE INVENTION

1. Field of the Invention

The present invention relates to devices and methods for securing and retaining medical sensors in specific desired locations on the skin of a person, and in particular, to such sensor retention devices which provide enhanced adjustability of the positioning of the sensors.

2. Description of the Related Art

Modern medical techniques and instrumentation require the use of a wide variety of sophisticated sensors, one of which is a non-invasive pulse sensor. This type of sensor, e.g. using a piezoelectric element, is applied to the surface of the person's skin for detecting the person's pulse. Some means of retention is required to secure and retain the sensor at the desired location.

Various means of retention are well known and commonly used. Typically, these include various forms of elastic straps and adhesive tapes. However, such conventional sensor retention devices generally suffer from at least one of two common problems.

First, conventional sensor retention devices almost invariably require the use of two hands in their application. Thus, positioning and holding the sensor at a specific desired location, while simultaneously applying the sensor retention device, is virtually impossible.

Second, once the sensor has been securely positioned at the desired location, conventional sensor retention devices do not allow for slightly repositioning the sensor without upsetting the application of the sensor retention device and requiring that it be re-applied all over again.

SUMMARY OF THE INVENTION

An adjustable sensor retainer in accordance with the present invention provides a primary retainer means for initially and movably securing a sensor against a desired skin region of a person, and a secondary retainer means for finally and adjustably securing the sensor against the desired skin region. The primary retainer means comprises an adhesive tape strip for initially securing the sensor against the skin, wherein slight movement of the sensor is allowed for its being positioned in a specific desired location. The secondary retainer means comprises a tape strip which is selectively attachable to the top of the primary retainer means over the sensor. When attached, it applies increased pressure upon the sensor, thereby securing it in the final desired location. In a preferred embodiment of the present invention, the primary and secondary retainer means use mutually complementary hook and loop material for mutual removable attachment.

Further in accordance with the present invention, a remote adhesive exposure means is used for remotely exposing the adhesive on the adhesive tape strip of the primary retainer means. This allows the adhesive to be exposed while being positioned in the desired location on the skin surface. In a preferred embodiment, the remote adhesive exposure means comprises a blind side pull tab connected to a protective film covering the adhesive. The blind side pull tab is grasped and pulled from the blind side of the adhesive strip, i.e. the side opposite that having the adhesive, to remove the protective film. This provides for simplified one-handed tensioning of the adhesive tape strip and removal of the protective film while positioning and holding the sensor in place with the other hand.

These and other objective, features and advantages of the present invention will be understood upon consideration of the following detailed description of the invention and the accompanying drawings.

BRIEF DESCRIPTION OF THE DRAWINGS

FIG. 1 illustrates a preferred embodiment of an adjustable sensor retainer in accordance with the present invention.

FIG. 2 illustrates the application of the primary retainer means of the present invention embodiment of FIG. 1.

FIG. 3 illustrates the application of the secondary retainer means of the present invention embodiment of FIG. 1.

FIG. 4 illustrates the pull tab of the present invention embodiment of FIG. 1 as viewed along line 4—4 in FIG. 1.

FIG. 5 illustrates the application of an alternative embodiment of the secondary retainer means of the present invention.

FIG. 6 illustrates an alternative attachment technique for attaching a sensor to the primary retainer means of the present invention.

FIG. 7 illustrates an alternative embodiment of a primary retainer means in accordance with the present invention.

FIG. 8 illustrates a further alternative embodiment of a primary retainer means in accordance with the present invention.

DETAILED DESCRIPTION OF THE INVENTION

Referring to FIG. 1, an adjustable sensor retainer 10 in accordance with the present invention, to which a pulse sensor 12 is attached, is illustrated. As shown, the pulse sensor 12 is typically connected via a signal interface 14 to some form of electronic instrumentation, such as a monitor 16. The sensor 12 is attached, e.g. adhesively affixed, at a sensor mounting zone 18 of the primary retainer means 20a, 20b of the sensor retainer 10.

The adjustable sensor retainer 10 comprises a primary retainer means 20a, 20b and a secondary retainer means 22. The primary retainer means 20a, 20b comprises similar individual retaining means 20a, 20b on either side of the sensor mounting zone 18. The following discussion will focus on one of these individual retaining means 20a and its associated elements and features, with the understanding that the other individual retaining means 20b and its associated elements and features can be similarly described.

The retaining means 20a comprises a single-sided adhesive strip 24 having an adhesive layer 26 on the bottom side thereof which is covered by a removable protective film 28. At the innermost end 30 of the protective film 28 is attached a remote adhesive exposure means. In the preferred embodiment illustrated in FIG. 1, this remote adhesive exposure means comprises a blind side pull tab 32a having a slit 34 through which the adhesive strip 24 (with its protective film 28) passes.

When the blind side pull tab 32a is at its innermost position along the adhesive strip 24, i.e. at its closest to the sensor mounting zone 18 as shown in phantom in FIG. 1, the protective film 28 substantially covers the adhesive layer 26. As the blind side pull tab 32a is pulled outwardly away from the sensor mounting zone 18, the protective film 28 is pulled away from the adhesive layer 26, curling downwardly as shown. As should be evident from FIG. 1, as the blind side pull tab 32a is removed further outwardly along the adhesive strip 24, the protective film 28 will ultimately become entirely removed, thereby fully exposing the adhesive layer 26. As discussed more fully below, this allows the retaining means 20a to be adhesively applied to the skin of a person (not shown) for securing and retaining the sensor 12, as desired.

The secondary retainer means 22, as discussed more fully below, is used to finally secure and retain the sensor 12 in its desired location, as well as to allow for subsequent repositioning of the sensor 12. In the preferred embodiment of FIG. 1, the secondary retainer means 22 comprises a tape strip to which the hook portion of hook and loop material (e.g. Velcro ®) is included on its lower surface 36. The material on this surface 36 engages with two pieces 38a, 38b of its material complement (e.g. loop material) included on the upper surfaces of the individual retaining means 20a, 20b.

Referring to FIG. 2, application of the primary retainer means 20a, 20b to the skin of a person can be better understood. The sensor 12 is initially positioned and held over a desired location 40 on the skin of a person. As the sensor 12 is held in position with one hand, the individual retaining means 20a can be applied with the other hand, as shown. The blind side pull tab 32a is removed outwardly away from the sensor 12, thereby outwardly tensioning the retaining means 20a and causing the protective film 28 to be removed from the adhesive layer 26. Downward pressure can be applied against, i.e. transferred to, the adhesive strip 24 via the upper edge of the slit 34 of the blind side pull tab 32a, as desired, to impress the adhesive layer 26 against the skin area 42 distal from that skin region 40 immediately below the sensor 12. With the primary retainer means 20a, 20b now fully applied, the sensor 12 is now initially positioned at its desired location. The sensor 12 can then be slightly repositioned to the exact, specifically desired location, as desired, due to the inherent flexibility of the tape areas 19a, 19b adjacent to the sensor mounting zone 18 of the primary retainer means 20a, 20b. Once the sensor 12 is positioned exactly as desired, the secondary retainer means 22 can be applied, as discussed below.

Referring to FIG. 3, it can be better understood how the secondary retainer means 22 finally secures and retains the sensor 12 in the desired location. The secondary retainer means 22 is pulled taut over and across the primary retaining means 20a, 20b, which in turn, is holding the sensor 12 in place. The mutually complementary pieces of hook and loop material 36, 38a are engaged, thereby securing the secondary retainer means 22 to the retaining means 20a, as shown.

Referring to FIG. 4, the blind side pull tab 32a can be better seen and understood. As discussed above, the blind side pull tab 32a has a slit 34 through which the adhesive strip 24, with its adhesive layer 26 and protective film 28, is passed. The end 30 of the protective film 28 can be attached to the blind side pull tab 32a by any of numerous conventional means (e.g. glue).

Referring to FIG. 5, an alternative preferred embodiment of the secondary retainer means 22 is illustrated in its taut, engaged position. In this embodiment, the secondary retainer means 22 uses a layer of adhesive 44 to achieve its attachment to the primary retainer means 20a, 20b. In other words, rather than engaging pieces of mutually complementary hook and loop material, the secondary 22 and primary 20a, 20b retainer means can be mutually attached via a layer of adhesive 44.

It should be understood that any of several conventional types of flexible tape material can be used for the primary 20a, 20b and secondary 22 retainer means. For example, Tyvek ®, vinyl, hook and loop (e.g. Velcro ®), paper or cloth tape can be used. It should be further understood that any of several conventional types of adhesive material, such as acrylic, gum or silicone, can be used. The protective film 28 preferably comprises any conventional form of wax or silicone coated paper (i.e. non-stick), and the blind side pull tab 32a preferably comprises cardboard.

It should be further understood that the secondary retainer means 22 can be removably attached to the primary retainer means 20a, 20b according to other attachment techniques known in the art. For example, the secondary retainer means 22 can have hook material on its lower surface 36, as discussed above, while the upper surface of the adhesive strip 24 comprises a textured material, such as a loosely woven fabric (e.g. cotton or gauze). Further, the secondary retainer means 22 can be attached to the primary retainer means 20a, 20b in such a manner as to permanently attach one end thereof to the primary retainer means 20a, 20b (e.g. via gluing, sewing, etc.), thereby leaving the other end removably attachable for use as discussed above.

Referring to FIG. 6, an alternative means of attaching the sensor 12 to the sensor mounting zone 18 of the primary retainer means 20a, 20b is shown. In this embodiment, the sensor 12 is movably attached to the sensor mounting zone 18 by including a clip 46 on the sensor 12, through which the sensor mounting zone 18 of the primary retainer means 20a, 20b is free to move. This embodiment can allow increased lateral movement of the sensor 12 after its initial positioning by the application of the primary retainer means 20a, 20b, as discussed above.

Referring to FIG. 7, an alternative embodiment of the remote adhesive exposure means is illustrated. Rather than a blind side pull tab 32a, as discussed above, this embodiment comprises a pull tab 48 having a transverse member 50, over which the adhesive strip 24 is rolled successively back onto itself. In other words, the adhesive strip 24 is rolled successively back onto itself inwardly toward the sensor mounting zone 18, thereby forming a transverse core 52 through which the transverse member 50 of the pull tab 48 passes. The adhesive layer 26 becomes exposed as the pull tab 48 is pulled outwardly away from the sensor 12. This embodiment may be more desirable than that using the blind side pull tab 32a and protective film 28, as discussed above, for the purposes of economy.

Referring to FIG. 8, a further alternative embodiment of the remote adhesive exposure means is illustrated. In this embodiment, an adhesive backing strip 54, having an adhesive layer 56, is applied over the top of the primary adhesive strip 24. This combination of backing 54 and adhesive 24 strips is then rolled back onto itself inwardly from the outermost end 58, similar to the embodiment illustrated in FIG. 7 and discussed above. The innermost end 60 of the backing strip remains exposed for grasping by doubling back its adhesive layer, as shown. Thus, by grasping the exposed end 60 of the backing strip 54 and pulling outwardly away from the sensor 12, the adhesive strip 24 is extended and its adhesive layer 26 becomes exposed for application to the person's skin (not shown), as discussed above.

It should be appreciated that the remote adhesive exposure means, as discussed above, will have other potential applications for other devices using adhesive strips. For example, including remote adhesive exposure means according to the present invention (e.g. blind side pull tabs) on adhesive bandages (e.g. "band-aids") will facilitate their application to cuts or wounds.

It should be understood that various alternatives to the embodiments of the present invention described herein can be employed in practicing the present invention. It is intended that the following claims define the scope of the present invention, and that structures and methods within the scope of these claims and their equivalents be covered thereby.

What is claimed is:

1. An adhesive tape strip having a side with adhesive which is substantially concealed and a means for applying said tape strip while exposing said adhesive without touching said adhesive, said adhesive tape strip comprising:

a tape strip having a first side and a second side, wherein said first tape strip side has an adhesive layer which is substantially concealed and has a removable protective film with a first end and a second end; and remote adhesive exposure means for remotely exposing said adhesive layer from a position remote from said adhesive layer while simultaneously applying said adhesive layer to a contact surface, wherein said remote adhesive exposure means includes a blind side pull tab which is movably disposed generally adjacent to and longitudinally along said second tape strip side and is attached to said first protective film end;

wherein movement of said blind side pull tab along said tape strip toward said second protective film end causes removal of said protective film from said adhesive layer.

2. An adhesive tape strip as recited in claim 1, wherein said blind side pull tab includes a force pad which receives and transfers a force against said second tape strip side during said application of said adhesive layer to said contact surface.

* * * * *